United States Patent [19]

Hampton et al.

[11] Patent Number: 5,269,659
[45] Date of Patent: Dec. 14, 1993

[54] AIR SAMPLING PUMP SYSTEM

[75] Inventors: Gary A. Hampton; Patrick R. Zimmerman, both of Boulder, Colo.

[73] Assignee: University Corporation for Atmospheric Research, Boulder, Colo.

[21] Appl. No.: 937,534

[22] Filed: Aug. 28, 1992

[51] Int. Cl.$^5$ .................................... F04B 49/06
[52] U.S. Cl. ................................ 417/12; 417/43; 417/45; 417/53
[58] Field of Search ............... 417/12, 43, 44, 45, 417/53

[56] References Cited

U.S. PATENT DOCUMENTS

| | | | |
|---|---|---|---|
| 2,408,851 | 10/1946 | Hillier | 417/43 |
| 4,063,824 | 12/1977 | Baker et al. | 417/63 |
| 4,397,610 | 8/1983 | Krohn | 417/44 |
| 4,552,513 | 11/1985 | Miller et al. | 417/53 |
| 4,756,670 | 7/1988 | Arai | 417/43 |
| 4,781,536 | 11/1988 | Hicks | 417/53 |
| 5,163,818 | 11/1992 | Betsill et al. | 417/20 |

OTHER PUBLICATIONS

Humphries, James T. and Sheets, Leslie P., Industrial Electronics, 3rd edition, 1989 pp. 293-296.

Primary Examiner—Richard A. Bertsch
Assistant Examiner—David W. Scheuermann
Attorney, Agent, or Firm—Duft, Graziano & Forest

[57] ABSTRACT

A pump is driven by a pump motor drive circuit that produces a series of pulse width modulated signals. A closed loop system is included to provide data indicative of any variation in the fluid flow. This is accomplished by using a Venturi located in the fluid flow path to create a pressure differential indicative of the fluid flow. A pressure transducer electronically measures this pressure differential which is then compared to a reference pressure differential indicative of the desired fluid flow. Any variation between the measured and desired fluid flow causes the pump motor drive circuit to vary the width of the pulses that are transmitted to the pump motor.

17 Claims, 2 Drawing Sheets

AIR SAMPLING PUMP SYSTEM

GOVERNMENT FUNDED INVENTION

This invention was made with Government support under Agreement No. ATM-8709659 awarded by the National Science Foundation. The Government has certain rights in this invention.

FIELD OF THE INVENTION

This invention relates to pump systems, and, in particular, to a lightweight pump that provides a constant fluid flow in a fluid flow path independent of battery voltage, or obstructions in the air intake, or temperature variations, or wear of the pump mechanical components.

PROBLEM

It is a problem in the field of air sampling systems to store a precise quantity of air in an air sampling chamber in order to accurately determine the concentration of an identified component in the ambient atmosphere. In order to store an accurate measure of air, it is necessary to have a pump that draws the ambient air into the air sampling chamber at a constant flow over a predetermined period of time. Air sampling systems are generally carried aloft by a balloon and therefore must be simple in construction, lightweight, low in power consumption and inexpensive. The accuracy of the air samples taken by a typical air sampling system significantly impacted by obstructions in the air intake which cause a variation in the air flow that is provided to the air sampling chamber. Additional factors that cause variation in air flow are mechanical wear of the pump components, fluctuations in the battery voltage and thermal variations in the system. Prior air sampling systems generally do not compensate for these factors and the component concentration measurements taken on the stored air sampled are therefore prone to a certain degree of error.

SOLUTION

The above described problems are solved and a technical advance achieved in the field by the constant flow pump system of the present invention. This system uses a pump whose motor is driven by a pump motor drive circuit that produces a series of pulse width modulated drive signals. A closed loop servo circuit is included to provide data indicative of impact of various environmental conditions on the fluid flow through the pump. A control circuit dynamically compensates for these variables in order to maintain a constant fluid flow in the fluid flow path. This is accomplished by varying the width of the drive signal pulses that are transmitted to the pump motor by the pump motor drive circuit. By varying the width of the drive signal pulses, the speed of the motor and therefore the fluid flow can be very precisely controlled. The control circuit is simple, accurate and inexpensive, to enable the use of an inexpensive pump in an application such as an air sampling system, since any inaccuracy in the operation of the pump is automatically compensated for by the closed loop servo circuit.

The flow of air into an air sampling chamber in a typical air sampling system is affected by numerous variables, such as battery voltage, obstructions in the air flow path, mechanical wear of the pump elements and temperature variations. The effects of all of these factors are manifested in a single end result, that is, a variation in the air flow through the pump. The air sampling pump system concurrently compensates for all of these factors by monitoring the air flow in the air flow path, such as into the air sampling chamber, and dynamically varying the speed of operation of the pump in order to maintain a constant air flow. This is accomplished by using a Venturi located in the flow path, such as at the pump output to create a pressure differential indicative of the air flow into the air sampling chamber. A pressure transducer is used to electronically measure this pressure differential, which is compared to a reference pressure differential indicative of the desired air flow. Any variation between the measured and desired air flows causes the pump motor drive circuit to vary the width of the drive signals pulses that are transmitted to the pump motor. By using pulse width modulated signals to control the speed of motor operation, the air flow produced by the pump can be very precisely controlled without the need for expensive flow control apparatus.

DETAILED DESCRIPTION

Air sampling systems are used to collect air samples a predetermined distance above ground level to measure certain environmental components contained in the atmosphere. The air sampling system is carried aloft by a balloon that is tethered at a predetermined location. The air sampling system can include one or more air sampling chambers that are used to store the air samples. A battery operated pump system is included in the air sampling system to draw a predetermined amount of ambient air into the air sampling chamber on a periodic basis. The pump system is activated either by radio signals or a timer to take a number of air samples over a period of time. The balloon is then retrieved and the air samples stored in the air sampling chambers are analyzed in a laboratory to measure the concentration of the desired component contained in the stored air samples.

It is obvious that the accuracy of these measurements is a function of the precision with which a predetermined quantity of air can be stored in the air sampling chamber. Any significant variations in the quantity of air stored in the air sampling chamber significantly impacts the accuracy of the component readings taken. In order to provide this accuracy, air sampling systems typically make use of expensive pumps which operate with a high degree of regularity to pump a very precise air flow into the air sampling chamber. A difficulty with these pumps is that they are fairly expensive and consume a significant amount of energy during operation, thereby necessitating a shortened sampling time or a larger component of batteries to provide power. Even with the use of an expensive pump, variations in the air samples can occur due to temperature fluctuations which vary the operation of the pump as well as obstructions which may partially block the air intake, thereby corrupting the readings taken by the air sampling system.

Air Sampling Pump System

In order to overcome these problems, the constant flow pump system of the present invention makes use of an inexpensive, lightweight pump whose operation can be of lesser accuracy than the pump systems of the prior art. Any fluctuation in fluid pumping rate, as well as all the other environmental factors that can affect air sampling accuracy, are dynamically and concurrently compensated for by the closed loop servo system of the air sampling pump system. The pump motor is an electric motor driven by a pump motor drive circuit that produces a series of pulse width modulated pulses to drive the pump motor. The use of a pulse width modulated drive signal enables the pump motor drive circuit to very precisely regulate the speed of rotation of the pump motor and therefore the flow rate of the pump system. The speed of pump motor operation is related to the duty cycle of the pulses applied to the windings thereof.

Figure 1:
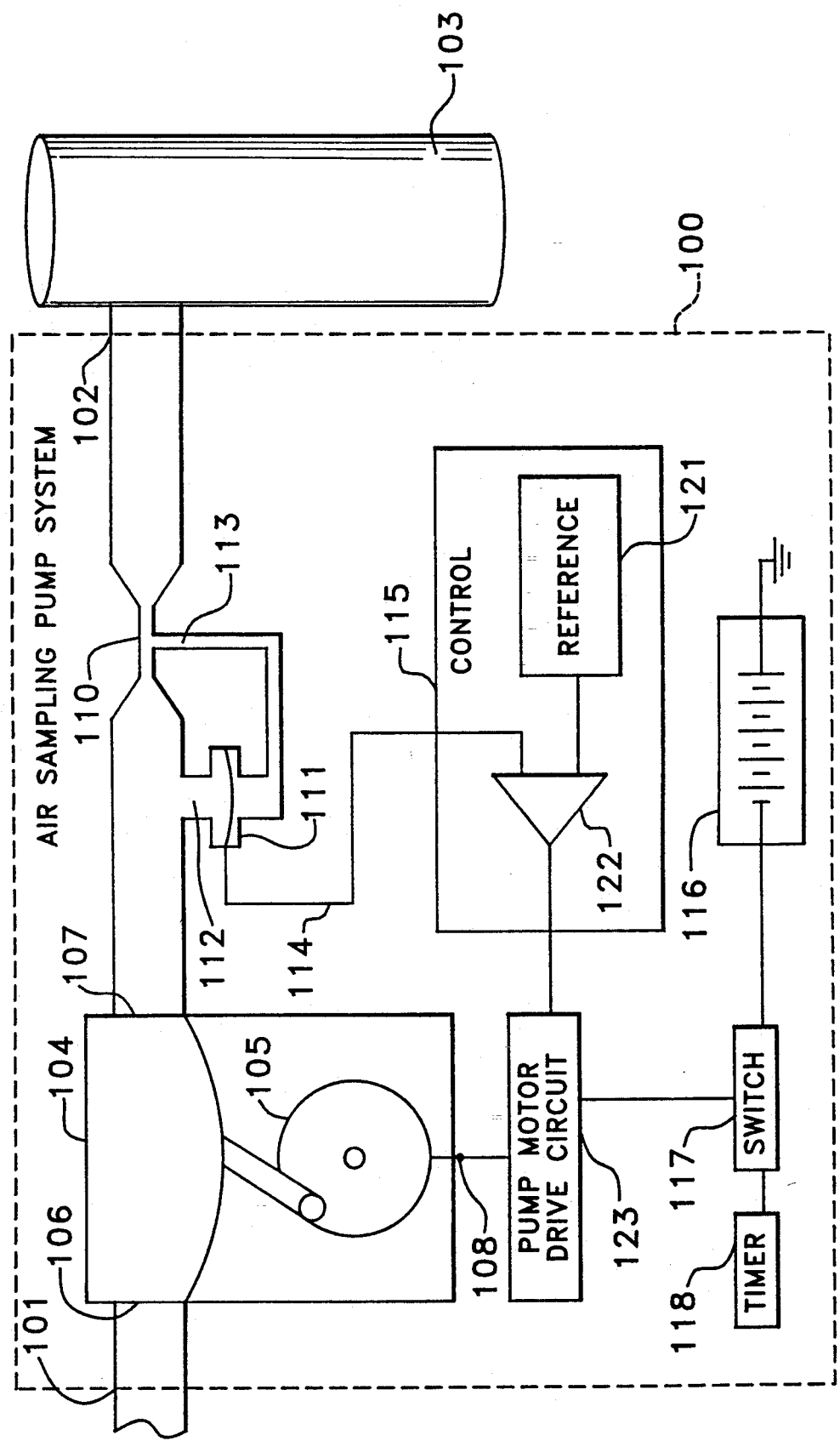
FIG. 1 illustrates in block diagram form an air sampling pump system to illustrate the concepts of the present invention.

FIG. 1 illustrates in block diagram form the overall architecture of the air sampling pump system 100 of the present invention. The pump 104 has an input port 106 connected to an air inlet 101 which provides access to the ambient air. The output port 107 of the pump 104 is applied through a Venturi 110 to an output pipe 102 which connects the pump system 100 to one or more air sampling chambers 103. The Venturi 110 is a narrow length of tubing which dramatically restricts the diameter of the air flow path at the pump output port 107 for a short length of the air flow path. This Venturi 110 causes the fluid velocity to increase as it passes through the restriction. Because of the law of conservation of energy, the pressure in the restriction is reduced proportionately. The precise nature of this pressure differential between the Venturi 110 and the pump output port 107 is described by Bernoulli's equation. The pressure differential increases if the ratio of the tube areas increases or if the fluid flow increases. The Venturi tube 110 is ducted to deliver a high pressure from the large diameter portion of the Venturi 110 through a first outlet 112 to one side of a differential pressure transducer 111 while delivering the low pressure from the narrow portion of the Venturi 110 through a second outlet 113 to the other side of the differential pressure transducer 111. The output 114 of the differential pressure transducer 111 produces a voltage that is proportional to the pressure differential as measured in the Venturi 110. The Venturi 110 can be installed at various locations in the fluid flow path and the location of FIG. 1 is simply illustrative.

Pump Control Circuits

The pump control circuits include a timer activated power source 116-118 which periodically activates the air sampling pump system 100 for a predetermined duration. A pump motor drive circuit 123 is provided to controllably power the pump motor 105 as regulated by control circuit 115. Pressure transducer 111 and control circuit 115 provide the closed loop servo control system that precisely regulates the speed of operation of pump motor 105 and thereby the air flow into air sampling chambers 103 via output pipe 102.

The output 114 of the differential pressure transducer 111 is connected to control circuit 115, which includes differential amplifier 122. The voltage that appears on transducer output 114 is applied to one input of the differential amplifier 122 while the other input of the differential amplifier 122 is connected to the output of a flow rate reference device 121. The flow rate reference device 121 delivers a reference voltage indicative of a reference pressure differential which is in turn indicative of the desired fluid flow. The differential amplifier 122 compares the two voltages and adjusts its output according to this comparison. If the voltage on transducer output 114 is less than the reference signal from flow rate reference device 121, the amplifier 122 increases its output to cause the pump motor drive circuit 123 to apply more power to the pump motor 105. If the voltage on transducer output 114 is more than the reference signal from flow rate reference device 121, the amplifier 122 reduces its output, thereby reducing the power supplied to the pump motor 105. The flow rate reference circuit 121 consists of a reference voltage source that outputs a very precise output voltage indicative of the desired fluid flow. This fluid flow value is preset prior to activation of the air sampling pump system or can be switched between a plurality of values if a number of different fluid flow rates are desired. In most applications, the flow rate reference circuit 12 produces a fixed value voltage of a great precision to cause a constant air flow to be applied to the air sampling chamber 103. A battery 116 is provided to supply power to the pump motor drive circuit 123, the control circuit 115 and to the pump motor 105. A timer 118 is used in a typical application to periodically activate the pump motor 105, control circuit 115, and pump motor drive circuit 123 to take air samples on a periodic basis. The timer 118 activates a power switch 117, such as a transistor, to apply power from the battery 116 to the pump motor drive circuit 123 as well as the control circuit 115 comprising the differential amplifier 122 and flow rate reference circuit 121. The pump motor drive circuit 123 consists of a pulse width modulator, the frequency of operation of which is fixed at a predetermined value. The input to the pulse width modulator, provided by the differential amplifier 122, is used to vary the width of the pulses produced by this circuit. The pulse width modulated signals produced by the pump motor drive circuit 123 are applied to the pump motor 105 to regulate the speed of operation of the motor 105.

The pulse width modulator used to implement pump motor drive circuit 123 produces pulses of predetermined frequency and a nominal width. The signal output by differential amplifier 122 varies the width of the pulses output by the pulse width modulator. The differential amplifier 122 can output a nominal output voltage which sets the nominal pulse width or can produce an output voltage only when a variation in pressure differential is detected. In either case, the combination of differential amplifier 122/pulse width modulator 123 operates to translate a discrepancy in fluid flow, as measured by a variation in pressure differential from a desired value, into a modification of operating speed of the pump motor 105.

Method of Operation

Figure 2:
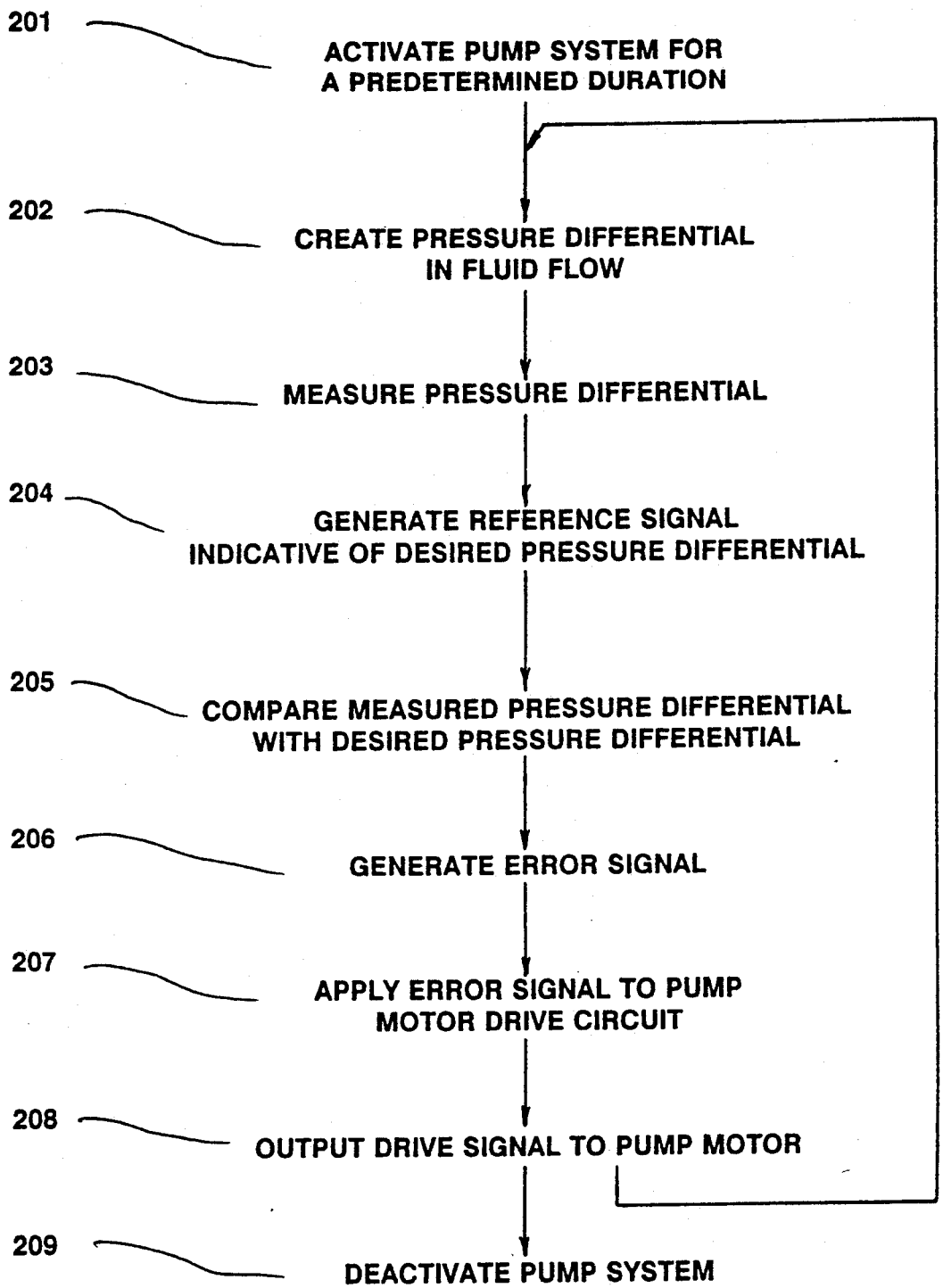
FIG. 2 illustrates in flow diagram form the operational steps taken by the air sampling pump system to maintain a constant air flow into the air sampling chamber.

In operation, at step 201 (FIG. 2) the timer 118 periodically activates switch 117 to apply power from battery 116 to pump motor drive circuit 123, control circuit 115, and transducer 111 for a predetermined duration of time. The volume of fluid stored in sampling chamber 103 is a function of the fluid flow output by pump system 100 via output pipe 102 and the length of time the pump system 100 is activated. The timer 118 precisely controls the length of time pump system 100 is active and disabled.

Control of the fluid flow output by pump system 100 at output pipe 102 is accomplished by creating a pressure differential at step 202. The pressure differential is produced via Venturi 110 and measured at step 203 with differential pressure transducer 111. A reference signal is produced by flow rate reference circuit 121 at step 204 to indicate a desired pressure differential, which is directly related to the desired fluid flow. At step 205, differential amplifier 122 compares the measured pressure differential from pressure transducer 111 with the desired pressure differential from flow reference circuit 121 to produce, at step 206, an error signal at its output indicative of the magnitude and direction of the variation in fluid flow. The error signal is applied at step 207 to pulse motor drive circuit 123 to regulate the drive signal applied to pump motor 105. The pulse width modulator circuit in pulse motor drive circuit 123 varies the width of the pulses produced in response to the magnitude and sign of the error signal. At step 208 the generated drive signals are applied to pump motor 105 to drive the pump.

This cycle continuously runs until the timer deactivates the pump system 100 at step 209 when the predetermined duration has elapsed. The closed loop servo system implemented in steps 202-208 functions to produce a constant fluid flow by driving the measured pressure differential to equal the desired or reference pressure differential via control of the pump motor operating speed.

SUMMARY

Therefore, the Venturi/pressure transducer combination provides a measure of the fluid flow into the air sampling chamber 103. This apparatus, in combination with the differential amplifier and the reference voltage generator, provides a closed loop servo system to regulate the speed of the pump operation as controlled by the pulse width modulator circuit that functions as the pump motor drive circuit. This closed loop feedback system, using pulse width modulated speed control for the pump motor, provides far greater flow rate precision control than prior art systems.

While a specific embodiment of this invention has been disclosed, it is expected that those skilled in the art can and will design alternate embodiments of this invention that fall within the scope of the appended claims.

We claim:

1. A pump system, having an input and an output, for producing a precisely controlled flow of fluid in a fluid flow path, comprising:
   a fluid flow path from said pump system input to said pump system output, including pump means, having an input connected to said pump system input, and an output connected to said pump system output for creating a fluid flow in said fluid flow path;
   means for generating a control signal indicative of a fluid flow at a predetermined location in said flow path; and
   means, responsive to said control signal, for regulating operating speed of said pump means as a function of said control signal, comprising:
   pump drive means for applying periodic pulses to said pump means to establish an operating speed of said pump means;
   means for generating a reference signal of predetermined value indicative of a predetermined fluid flow;
   means for producing an error signal indicative of a measured difference between said control signal and said reference signal; and
   wherein said pump drive means is responsive to said error signal for adjusting said operating speed of said pump means to compensate for a difference between said measured fluid flow and said predetermined fluid flow by adjusting a width of said periodic pulses.

2. The apparatus of claim 1 wherein said generating means comprises:
   a Venturi tube, ducted to a first outlet and a second outlet, connected in said flow path such that fluid flowing in said flow path flows through said Venturi tube; and
   means for generating a control signal indicative of a pressure differential between said first outlet and said second outlet.

3. The apparatus of claim 1 wherein said pump drive means comprises a pulse width modulator circuit for applying said periodic pulses, whose width is a function of said error signal, to said pump means.

4. The apparatus of claim 1 further comprising:
   means for periodically enabling said pump means for a predetermined duration.

5. A pump system, having an input and an output, for producing a fluid flow in a fluid flow path comprising:
   a fluid flow path from said pump system input to said pump system output including an electrically operated pump, having power input terminals, a fluid input port connected to said pump system input and an output port connected to said pump system output for creating a fluid flowing said fluid flow path;
   means, connected in said fluid flow path, for measuring said fluid flow;
   means for generating a control signal indicative of a difference between said measured fluid flow and a desired fluid flow, comprising;
   means for producing a reference signal of constant value indicative of a desired pressure differential; and
   means for generating said control signal indicative of a difference between said measured pressure differential and said desired pressure differential as measured by a difference between said measurement signal and said reference signal; and
   means, connected to said power input terminals and responsive to said control signal, for applying a drive signal to said power input terminals to control operating speed of said pump, comprising;
   means for producing periodic pulses, the width of which are a function of said control signal.

6. The apparatus of claim 5 further comprising:
   means for periodically enabling said pump for a predetermined duration.

7. The apparatus of claim 5 wherein said applying means further comprises:
   means for varying the width of said pulses from said nominal width by an amount related to a magnitude of said control signal.

8. The apparatus of claim 5 wherein said measuring means comprises a Venturi interposed in said fluid flow path for creating a pressure differential indicative of said fluid flow.

9. The apparatus of claim 8 wherein said measuring means further comprises:
    transducer means for producing or measurement signal indicative of said pressure differential.

10. A method of controlling the flow of fluid in a fluid flow path having an input and an output, including a pump having an input connected to said fluid flow path input and an output connected to said fluid flow path output to create a fluid flow in said fluid flow path, comprising the steps of:
    generating a control signal indicative of a fluid flow at a predetermined location in said fluid flow path; and
    regulating, in response to said control signal, operating speed of said pump as a function of said control signal, comprising;
    applying periodic pulses to said pump to establish an operating speed of said pump;
    generating a reference signal indicative of a predetermined fluid flow;
    producing an error signal indicative of a measured difference between said control signal and said reference signal; and
    adjusting said operating speed of said pump to compensate for a difference between said measured fluid flow and said predetermined fluid flow.

11. The method of claim 10 wherein said fluid flow path includes a Venturi tube, ducted to a first outlet and a second outlet, connected in said fluid flow path such that fluid flowing in said fluid flow path flows through said Venturi tube, said step of generating comprises:
    generating a control signal indicative of a pressure differential between said first outlet and said second outlet.

12. The method of claim 10 wherein said step of adjusting further comprises:
    applying, using a pulse width modulator, periodic pulses, whose width is a function of said error signal, to said pump.

13. The method of claim 10 further comprising the step of:
    periodically enabling said pump for a predetermined duration.

14. A method of controlling a fluid flow in a fluid flow path having an input and an output, including an electrically powered pump, which has an input connected to said fluid flow path input and an output connected to said fluid flow path output for creating a fluid flow, comprising the steps of:
    creating a pressure differential in said fluid flow path to measure said fluid flow;
    measuring said pressure differential;
    comparing said measured pressure differential with a desired pressure differential, comprising:
    producing a reference signal of constant value indicative of a desired pressure differential; and
    generating said control signal indicative of a difference between said measured pressure differential and said desired pressure differential as measured by a difference between said measurement signal and said reference signal; and
    regulating, in response to said comparison, operating speed of said pump to minimize a difference between said measured pressure differential and said desired pressure differential, comprising:
    producing periodic pulses, the width of which are a function of said control signal.

15. The method of claim 14 wherein said step of regulating further comprises:
    adjusting a width of said pulse width modulated signals as a function of said comparison.

16. The method of claim 14 further comprising the step of:
    periodically enabling said step of regulating for a predetermined duration.

17. The method of claim 14 further comprising the step of:
    periodically disabling said pump for a predetermined duration.

* * * * *